(12) United States Patent
Jo et al.

(10) Patent No.: US 10,849,882 B2
(45) Date of Patent: Dec. 1, 2020

(54) USE OF CARBAMATE COMPOUND FOR PREVENTING OR TREATING FIBROMYALGIA OR FUNCTIONAL SYNDROME ASSOCIATED WITH FIBROMYALGIA

(71) Applicant: SK BIOPHARMACEUTICALS CO., LTD., Gyeonggi-do (KR)

(72) Inventors: Min Jae Jo, Gyeonggi-do (KR); Han Ju Yi, Gyeonggi-do (KR); Sun Gwan Hwang, Gyeonggi-do (KR)

(73) Assignee: SK BIOPHARMACEUTICALS CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/302,858

(22) PCT Filed: May 18, 2017

(86) PCT No.: PCT/KR2017/005173
§ 371 (c)(1),
(2) Date: Nov. 19, 2018

(87) PCT Pub. No.: WO2017/200318
PCT Pub. Date: Nov. 23, 2017

(65) Prior Publication Data
US 2019/0298694 A1    Oct. 3, 2019

(30) Foreign Application Priority Data

May 19, 2016    (KR) .......................... 10-2016-0061392

(51) Int. Cl.
| A61K 31/41 | (2006.01) |
| A61K 9/00 | (2006.01) |
| A61K 31/16 | (2006.01) |
| A61P 29/00 | (2006.01) |
| A61P 21/00 | (2006.01) |
| A61P 25/00 | (2006.01) |

(52) U.S. Cl.
CPC ................ *A61K 31/41* (2013.01); *A61K 9/00* (2013.01); *A61K 31/16* (2013.01); *A61P 21/00* (2018.01); *A61P 25/00* (2018.01); *A61P 29/00* (2018.01)

(58) Field of Classification Search
CPC .................................................... A61K 31/41
See application file for complete search history.

(56) References Cited

U.S. PATENT DOCUMENTS

| 3,415,840 | A | 12/1968 | Wolf | |
| 2006/0258718 | A1* | 11/2006 | Choi | .................... C07D 249/04 514/359 |
| 2010/0323410 | A1 | 12/2010 | Lim et al. | |
| 2011/0111467 | A1 | 5/2011 | Lim et al. | |

FOREIGN PATENT DOCUMENTS

| KR | 101286499 B1 | 7/2013 |
| WO | WO-2006/112685 A1 | 10/2006 |
| WO | WO-2010/150946 A1 | 12/2010 |
| WO | WO-2011/046380 A2 | 4/2011 |

OTHER PUBLICATIONS

Nijs et al., How to explain central sensitization to patients with "unexplained" chronic musculoskeletal pain: Practice guidelines, 2011, Manual Therapy, 16, pp. 413-418 (Year: 2011).*
Bennett, R.M. (2009) "Clinical Manifestations and Diagnosis of Fibromyalgia.", *Rheum Dis Clin N Am.*, 35:215-232. (doi:10.1016/j.rdc.2009.05.009).
Clauw, D. J. (2015) "Fibromyalgia and Related Conditions.", *Mayo Clin Proc.*, 90(5):680-692, (May 2015).
Chaplan, et al. (1994) "Quantitative assessment of tactile allodynia in the rat paw.", *Journal of Neuroscience Methods*, 53:55-63.
Dixon, W.J. (1980) "Efficient Analysis of Experimental Observations.", *Ann. Rev. Pharmacal Toxicol.*, 20:441-62.
Sluka, et al. (2001) "Unilateral Intramuscular Injections of Acidic Saline Produce a Bilateral, Long-Lasting Hyperalgesia.", *Muscle Nerve*, 24:37-46. (Jan. 2001).
Karakurt, et al. (2001) "Synthesis of some 1-(2-naphthyl)-2-(imidazole-1-yl)ethanone oxime and oxime ether derivatives and their anticonvulsant and antimicrobial activities." *Eur. J. Med. Chem.*, 36(5):421-433.
International Search Report issued in International Patent Application No. PCT/KR2017/005173, dated Aug. 22, 2017, with English Translation.
Anonymous, "Novel Neurotherapeutics for Epilepsy, Neuropathic Pain and Bipolar Disorder", YKP3089, SK Biopharmaceuticals, Dec. 31, 2012, 16 pages.
Taylor, D. P., "YKP3089 (Epilepsy)—Poster", May 24, 2013, 1 page.
Bialer, M., et al.; "Progress report on new antiepileptic drugs: A summary of the Tenth Eilat Conference (EILAT X)" Epilepsy Research, 2010, 92, pp. 89-124.
Sumpton, J. E., et al.; "Chapter 33, Fibromyalgia", Neurologic Aspects of Systemic Disease Part I, 2014, vol. 122, pp. 513-527.
Extended European Search Report from corresponding European Patent Application No. 17799675.8, dated Dec. 18, 2019.

* cited by examiner

Primary Examiner — Kortney L. Klinkel
Assistant Examiner — Tori Strong
(74) *Attorney, Agent, or Firm* — Harness, Dickey & Pierce, P.L.C.

(57) ABSTRACT

The present invention relates to a pharmaceutical composition for preventing or treating fibromyalgia or a functional syndrome associated with fibromyalgia, the pharmaceutical composition comprising: a carbamate compound of chemical formula 1 or a pharmaceutically acceptable salt thereof, a solvate or a hydrate; and a pharmaceutically acceptable carrier. The pharmaceutical composition, according to the present invention, may enable the efficient treatment of fibromyalgia or a functional syndrome associated with fibromyalgia.

6 Claims, 2 Drawing Sheets

USE OF CARBAMATE COMPOUND FOR PREVENTING OR TREATING FIBROMYALGIA OR FUNCTIONAL SYNDROME ASSOCIATED WITH FIBROMYALGIA

CROSS-REFERENCE TO RELATED APPLICATIONS

This application is a national phase application of PCT Application No. PCT/KR2017/005173, filed on May 18, 2017, which claims priority to Korean Patent Application No. 10-2016-0061392, filed on May 19, 2016. The entire disclosure of the applications identified in this paragraph is incorporated herein by reference.

FIELD

The present invention relates to use of a carbamate compound of the following Formula 1 for the purpose of preventing or treating fibromyalgia or associated functional symptoms of fibromyalgia, by administering a pharmaceutical composition comprising said carbamate compound:

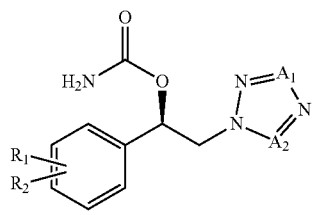

[Formula 1]

wherein,
$R_1$, $R_2$, $A_1$ and $A_2$ are as defined herein.

BACKGROUND

Fibromyalgia, also known as fibromyalgia syndrome, is a complex syndrome consisting of pain, such as central sensitization, hyperalgesia and spontaneous pain. Fibromyalgia is a chronic systemic pain disorder that is accompanied by various symptoms such as chronic fatigue, sleep disorder, cognitive disorder and depression. In particular, it often involves extensive pain, stiffness and tenderness in the musculoskeletal-related tissues, including muscles, tendons and ligaments (Bennett R M, Clinical manifestations and diagnosis of fibromyalgia, Rheum Dis Clin North Am., 2009; Clauw D J, Fibromyalgia and related conditions, Mayo Clin Proc., 2015).

Fibromyalgia has a prevalence rate of 2 to 8% according to diagnostic criteria. According to the diagnostic criteria published in 1990, fibromyalgia was diagnosed by the presence or absence of chronic systemic pain and a certain number of tender points (pain spots), and under these criteria fibromyalgia was much more prevalent in women than in men. According to the newly proposed standards in 2010 and 2011, the number of tender points (pain spots) is no longer included in the criteria for the diagnosis of fibromyalgia, and instead, various symptoms associated with chronic pain such as fatigue, sleeping disorder, cognitive disorder and depression are included in the criteria for the diagnosis. As a result, the number of male patients diagnosed with fibromyalgia increased, and the ratio of female to male patients changed from 9:1 in 1990 to 2:1 in the new standard.

Almost all of patients diagnosed with fibromyalgia experience chronic pain many times in different parts of the body for a lifetime, and pain experience at different parts of the body eventually leads to chronic systemic pain. Fibromyalgia often begins in childhood or adolescence, and patients diagnosed with fibromyalgia are likely to experience headache, menstrual irregularities, temporomandibular joint disorder, chronic fatigue, inflammatory bowel disease and other types of partial pain. In these patients, surgical treatment to remove partial pain does not result in successful pain relief. Fibromyalgia is a typical centralized pain, a pain situation that is distinctly different from nociceptive pain and neuropathic pain, which clinicians can rather easily distinguish.

The pathological mechanism of fibromyalgia is not fully understood until now, but it is believed that various environmental factors as well as genetic factors are involved. The probability of suffering from the same disease in families of patients diagnosed with fibromyalgia is 8.5 times higher than that of the general population. It was reported in certain studies of twins that about 50% of fibromyalgia is caused by genetic factors and about 50% by environmental factors. The main environmental factor that triggers the induction of fibromyalgia is a stress of various causes such as those that induce acute pain for several weeks. The onset of fibromyalgia is influenced by a variety of psychological, behavioral and social factors, and these various etiologic factors make treatment of the disease complicated.

A variety of pharmacological and non-pharmacological treatments have been used to treat fibromyalgia. Drugs such as tricyclic compounds, gabapentinoids and serotonin-norepinephrine reuptake inhibitors have been used for pharmacological treatment, and numerous drugs have been used in combination due to the complicated and various factors-involving pathogenesis of fibromyalgia.

Although various medicines have been adopted for the treatment of fibromyalgia, there is still a limitation on their use due to an unsatisfactory level of therapeutic effect or adverse effects because of complex pathologies accompanied by symptoms such as chronic fatigue and depression, as well as systemic musculoskeletal pain. Hence, there is still a need for new drugs with improved efficacy and fewer side effects.

DISCLOSURE

Problem to be Solved

The present invention is intended to provide a method for the prevention or treatment of fibromyalgia or associated functional symptoms of fibromyalgia.

The present invention is also intended to provide the use of a carbamate compound of the following Formula 1, or a pharmaceutically acceptable salt, solvate or hydrate thereof, for the prevention or treatment of fibromyalgia or associated functional symptoms of fibromyalgia:

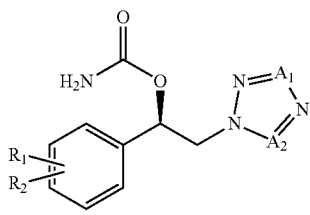

[Formula 1]

wherein, $R_1$, $R_2$, $A_1$ and $A_2$ are as defined herein.

Technical Solution to the Problem

The present invention provides a medicament for the prevention or treatment of fibromyalgia or associated functional symptoms of fibromyalgia, comprising a therapeutically effective amount of a carbamate compound of the following Formula 1, or a pharmaceutically acceptable salt, solvate or hydrate thereof:

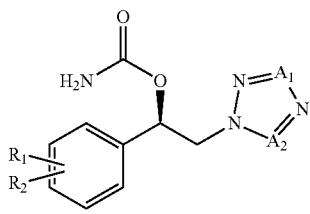

[Formula 1]

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prevention or treatment of fibromyalgia or associated functional symptoms of fibromyalgia, comprising a therapeutically effective amount of the carbamate compounds of the above Formula 1, or a pharmaceutically acceptable salt, solvate or hydrate thereof, and one or more of a pharmaceutically acceptable carrier.

In addition, the present invention provides a method for preventing or treating fibromyalgia or associated functional symptoms of fibromyalgia in a subject, comprising administering a therapeutically effective amount of the carbamate compounds of the above Formula 1, or a pharmaceutically acceptable salt, solvate or hydrate thereof to the subject.

In addition, the present invention provides the use of the carbamate compounds of the above Formula 1, or a pharmaceutically acceptable salt, solvate or hydrate thereof for the prevention or treatment of fibromyalgia or associated functional symptoms of fibromyalgia.

In one embodiment of the present invention, in the above Formula 1, R1 and R2 are each independently selected from the group consisting of hydrogen, halogen and C1-C8 alkyl.

In one embodiment, the halo C1-C8 alkyl is perfluoroalkyl.

According to another embodiment of the present invention, the carbamate compound of the above Formula 1 is carbamic acid (R)-1-(2-chlorophenyl)-2-tetrazol-2-yl)ethyl ester of the following Formula 2:

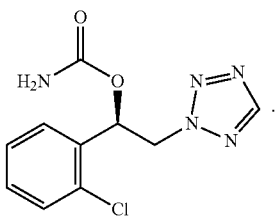

[Formula 2]

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the present invention can be chemically synthesized by any of the methods described in the above documents, but the methods are merely exemplary ones, and the order of the unit operation and the like may be selectively changed if necessary. Hence, the above methods are not intended to limit the scope of the invention.

The compounds of the present invention can be used for the prevention or treatment of fibromyalgia, and the fibromyalgia includes fibromyalgia syndrome.

According to one embodiment of the present invention, fibromyalgia may include fibromyositis, fibrositis, muscular rheumatism, musculoskeletal pain syndrome, non-articular rheumatism, pain due to rheumatoid muscularitis, tension myalgia, hyperalgesia, persistent pain, stiffness and tenderness.

In one embodiment, the compounds of the present invention can also be used for the prevention or treatment of associated functional symptoms of fibromyalgia. The associated functional symptoms of fibromyalgia may include headaches, insomnia, cognitive disorders, depression, body temperature abnormalities, irritable bowel syndrome, Sicca symptoms, hyperhidrosis (increased sweating), dizziness, tremor, dyspnoea, arrhythmias, paraesthesias, chronic fatigue and the like.

Musculoskeletal pain is a major feature of fibromyalgia, and animal models that are linked to musculoskeletal pain in humans can be used to assess the efficacy of therapeutic agents capable of treating fibromyalgia. For example, repeated injections of acidic saline into the gastrocnemius muscle of rats lead to mechanical allodynia due to central sensitization, which may well represent muscle pain or tenderness observed in patients with fibromyalgia (Sluka K A et. al., Unilateral intramuscular injections of acidic saline produce a bilateral, long-lasting hyperalgesia, Muscle Nerve. 2001).

The dosage of the present compounds for the prophylactic treatment of the disease may typically vary depending on the severity of the disease, the body weight and the metabolic status of the subject. A "therapeutically effective amount" for an individual patient refers to an amount of the active compound or pharmaceutical formulation sufficient to achieve the desired pharmacological effect, i.e., the prophylactic therapeutic effect as described above. The therapeutically effective amount of the compounds of the present invention is 50 to 500 mg, preferably 50 to 400 mg, more preferably 50 to 300 mg, and more preferably 50 to 200 mg, based on once-daily administration to humans.

The compounds of the present invention may be administered by a conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the present compounds, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydrabamine, hydrobromide, hydrochloride, hydrogencarbonate, hydroxynaphtoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, diethyleneamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention can be formulated such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skills can easily determine and prescribe dosages that are effective for the desired treatment or prophylaxis. The medicament or pharmaceutical composition according to one embodiment may be administered in one or more doses, for example, one to four times per day. The pharmaceutical composition according to one embodiment may contain 50 to 500 mg, preferably 50 to 400 mg, more preferably 50 to 300 mg, and more preferably 50 to 200 mg of the compound of Formula 1.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivative (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the term "subject" refers to an animal that is the object of prevention or treatment, preferably a mammal (e.g., primates (e.g., a human), cattle, sheep, goats, horses, dogs, cats, rabbits, rats, mice, etc.), most preferably a human.

As used herein, the terms "prevent," "preventing" and "prevention" refer to reducing or eliminating the likelihood of a disease.

As used herein, the terms "treat," "treating" and "treatment" refer to eliminating or alleviating a disease and/or its accompanying symptoms altogether or in part.

Effect of the Invention

The medicament and pharmaceutical composition according to the present invention can effectively prevent or treat fibromyalgia. In addition, the medicament and pharmaceutical composition according to the present invention can effectively prevent or treat associated functional symptoms of fibromyalgia.

DETAILED DESCRIPTION

Figure 1:
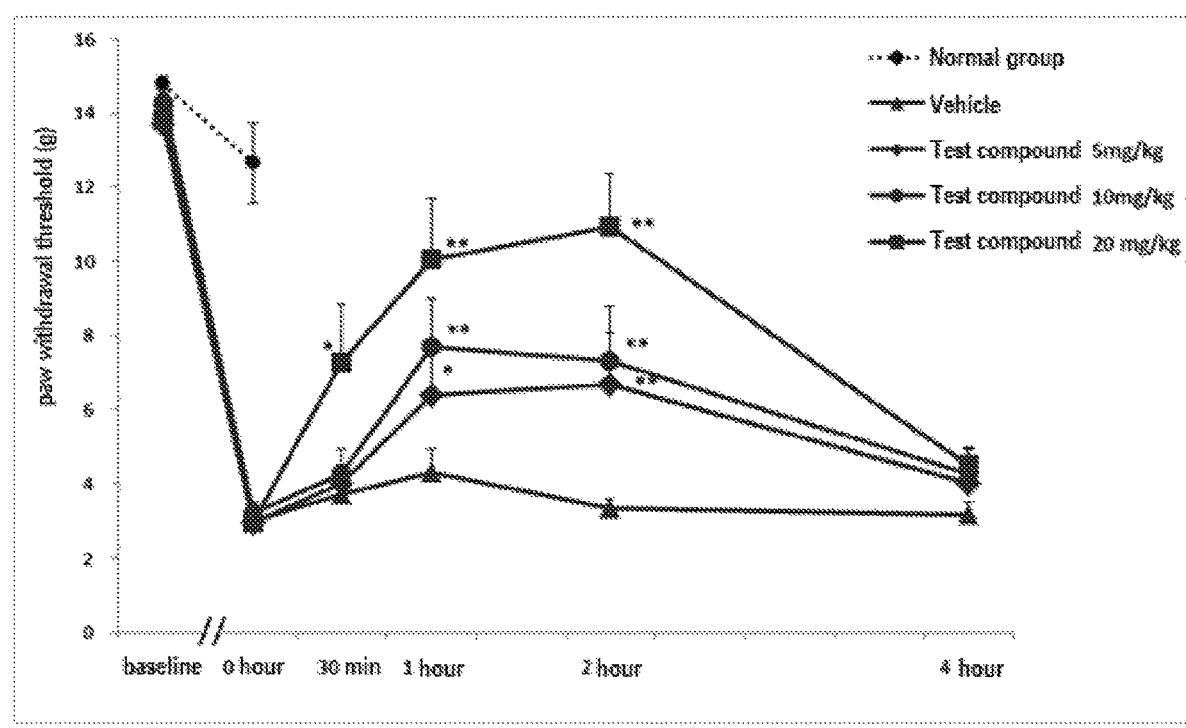
FIG. 1 shows the effect of carbamic acid (R)-1-(2-chlorophenyl)-2-tetrazol-2-yl)ethyl ester prepared in the following synthesis example (hereinafter referred to as "the test compound") on the reduction of the paw withdrawal threshold (PWT) to the stimulation of rat hind paw induced by administration of acidic saline (pH 4.0) into the right gastrocnemius muscle.
Figure 2:
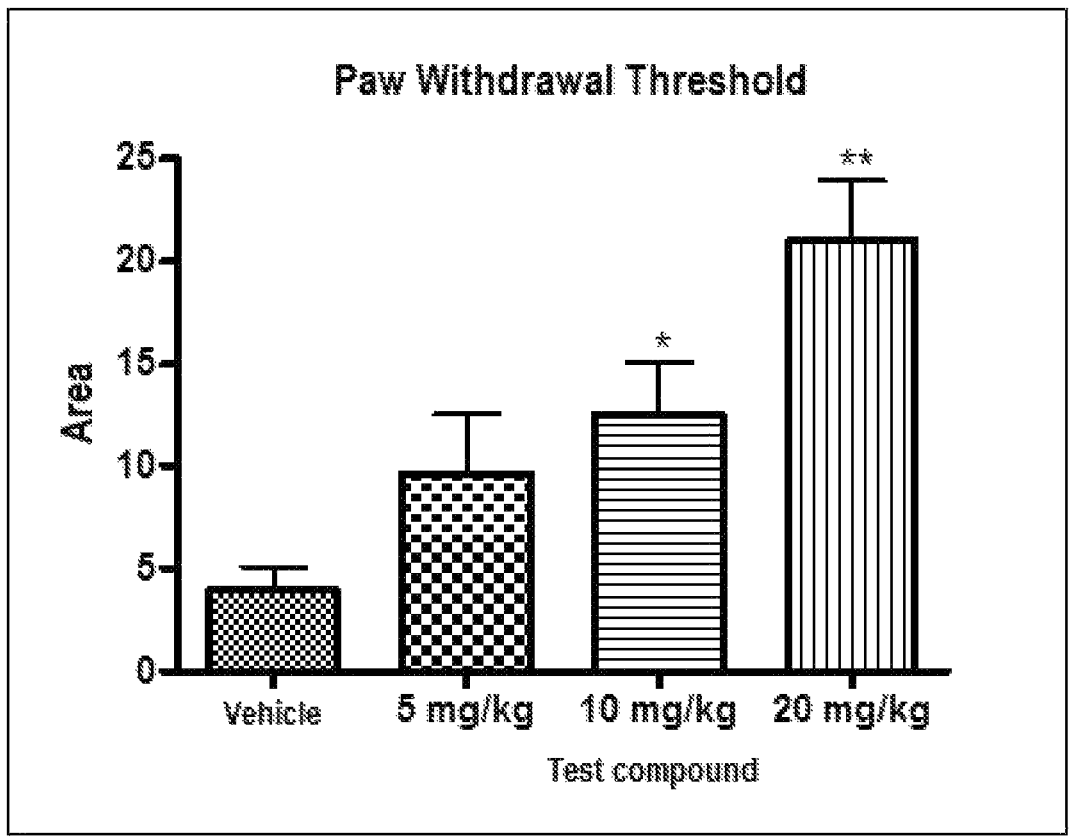
FIG. 2 is a graph showing the area under the curve of the paw withdrawal threshold curve for the test compound administration group in comparison with the vehicle group.

Hereinafter, the present invention will be explained in more detail through working examples. However, the following working examples are only intended to illustrate one or more embodiments and are not intended to limit the scope of the invention.

Synthesis Example: Synthesis of Carbamic Acid (R)-1-(2-chlorophenyl)-2-tetrazol-2-yl)ethyl ester Carbamic acid (R)-1-(2-chlorophenyl)-2-tetrazol-2-yl) ethyl ester was prepared according to the method described in Synthesis Example 50 of PCT Publication No. WO 2010/150946.

Example: Experiment of Pain Suppression Effect Using Animal Model of Fibromyalgia Musculoskeletal pain is a major feature of fibromyalgia. A model that is linked to musculoskeletal pain in humans has been developed by Sluka K A, which model is characterized by mechanical sensitization induced by repeated intramuscular injections of acidic saline.

This experiment evaluated the effect of the test compound on persistent mechanical allodynia, which may well represent muscle pain or tenderness observed in patients with fibromyalgia. Repeated injections of acidic saline into the gastrocnemius muscle of rats lead to mechanical allodynia due to central sensitization (Sluka K A et. al., Unilateral intramuscular injections of acidic saline produce a bilateral, long-lasting hyperalgesia, Muscle Nerve. 2001).

Experimental Animals

Male rats (Sprague-Dawley, 150-200 g, 6 weeks old, Orient Bio Co., Ltd.) were purchased and subjected to acclimatization for more than 1 week in an animal chamber. The experimental animals were maintained under conditions of light-and-darkness cycle of 12 hours, a temperature of 22 to 25° C., a relative humidity of 40 to 60%, and free access to water and food.

Measurement of Mechanical Allodynia

Mechanical allodynia was assessed by measuring the paw withdrawal threshold of the rat right hind paw using Dixon's "up-down method" (Chaplan et. al., Quantitative assessment of tactile allodynia in the rat paw. J Neurosci Methods, 1994; Dixon W J, Efficient analysis of experimental observations, Annu Rev Pharmacol Toxicol. 1980). First, the rats were placed in an acrylic box (13×25×13 cm3) located on a wire mesh installed at a height of about 35 cm from the floor and stabilized for more than 20 minutes. Eight (8) von Frey filaments with various bending forces (0.2, 0.4, 0.6, 1.0, 2.0, 4.0, 6.0, 8.0, 15.0 g) were used. Starting with a filament of 2.0 g, bending force was applied perpendicular to the sole surface. In the case of no withdrawal (avoidance response), the next higher bending force filament was applied, or, in the case of withdrawal (avoidance response), the next lower bending force filament was applied. In order to obtain at least six (6) response results, the application of filaments was proceeded four (4) more times after showing the change in withdrawal. Starting with a filament of 2.0 g, when the rats showed withdrawal (avoidance response) to the filaments four times in a row, 0.2 g was designated, and when the rats showed no withdrawal to the filaments five times in a row, 15.0 g was designated.

Induction of Mechanical Allodynia

The baseline withdrawal (avoidance response) threshold for mechanical stimulation on the right hind paw of rats was measured. 100 µl of preservative-free acidic saline (0.9% sodium chloride, pH 4.0) was intramuscularly injected into the right gastrocnemius muscle of the rats. After 5 days, the acidic saline was intramuscularly injected again into the same region by the same method. At 7 or 8 days after the second administration of acidic saline, induction of mechanical allodynia was confirmed by measuring withdrawal (avoidance response) thresholds to mechanical stimulation on the right hind paw, and rats with a mechanical withdrawal (avoidance response) threshold of less than 4.5 g were used for the evaluation of the test drug (Sluka K A et. al., Unilateral intramuscular injections of acidic saline produce a bilateral, long-lasting hyperalgesia, Muscle Nerve. 2001).

Administration

The test compound was prepared as a solution using 30% PEG 400 and 70% distilled water on a volume basis. Each solution was administered intraperitoneally to the rats at a volume of 3 ml per kg of rat. Withdrawal (avoidance response) thresholds to mechanical stimulation were measured at 30 minutes, 1 hour, 2 hours and 4 hours after drug administration.

Statistics

The effect of the compounds was expressed as mean±standard error, and the data were analyzed using one-way ANOVA and Dunnett's test, and compared by "% MPE (percent of maximum possible effect)." Statistical significance was recognized when data had a difference of $p<0.05$.

[% MPE=(threshold over time after drug treatment−threshold at 0 hour)/(threshold of normal group−threshold at 0 hour)×100]

As a result of two repeated injections of acidic saline, it was confirmed that the withdrawal (avoidance response) threshold to mechanical stimulation was significantly reduced compared to the normal group (compare the withdrawal thresholds at 0 hour in the normal group and the acidic saline administration group), which was similar to the existing results (Sluka K A et. al., Unilateral intramuscular injections of acidic saline produce a bilateral, long-lasting hyperalgesia, Muscle Nerve. 2001).

At 7 or 8 days after the second administration of acidic saline, withdrawal thresholds to mechanical stimulation (withdrawal threshold at 0 hour) were measured, and rats exhibiting a withdrawal threshold of less than 4.5 g were used for the evaluation of the pharmacological effect of the test compound. The vehicle or the test compound was administered intraperitoneally at doses of 5, 10 and 20 mg/kg, and withdrawal thresholds to mechanical stimulation were measured at 30 minutes, 1 hour, 2 hours and 4 hours.

As can be seen in Table 1 and FIG. 1, when the test compound was administered intraperitoneally at doses of 5, 10 and 20 mg/kg, the mechanical allodynia induced by repeated injections of acidic saline was significantly inhibited. In addition, as a result of calculating and analyzing the area under the curve of the paw withdrawal threshold curve over time, it was confirmed that the test compound showed a dose-dependent effect, and the 10 mg/kg, ip and 20 mg/kg, ip groups showed statistically significant effects compared with the vehicle group.

These results indicate that the test compound significantly reduces muscle mechanical hyperalgesia in a dose-dependent manner in the chronic myalgia model.

TABLE 1

Withdrawal (avoidance response) thershold to mechanical allodynia induced by injection of acidic saline into gastrocnemius muscle before and after the administration of the test compound[a]

|  |  | baseline[b] | 0 h | 30 min[c] | 1 h[c] | 2 h[c] | 4 h[c] |
|---|---|---|---|---|---|---|---|
| Normal group | Mean | 14.77 | 12.64 | — | — | — | — |
|  | SE | 0.23 | 1.07 | — | — | — | — |
| Vehicle | Mean | 14.41 | 2.99 | 3.73 | 4.29 | 3.32 | 3.18 |
| (N = 8) | SE | 0.59 | 0.45 | 0.45 | 0.63 | 0.26 | 0.30 |
| Test compound | Mean | 13.69 | 2.97 | 4.02 | 6.41[d] | 6.67[e] | 4.01 |
| 5 mg/kg | SE | 0.85 | 0.30 | 0.49 | 1.21 | 1.39 | 0.63 |
| (N = 7) | Effect (%) | — | — | 10.8 | 35.6 | 38.3 | 10.7 |
| Test compound | Mean | 14.29 | 3.20 | 4.27 | 7.68[e] | 7.30[e] | 4.26 |
| 10 mg/kg | SE | 0.58 | 0.31 | 0.66 | 1.32 | 1.48 | 0.66 |
| (N = 8) | Effect (%) | — | — | 11.4 | 47.5 | 43.5 | 11.3 |
| Test compound | Mean | 13.83 | 2.95 | 7.28[d] | 10.04[e] | 10.92[e] | 4.52 |
| 20 mg/kg | SE | 0.77 | 0.34 | 1.54 | 1.65 | 1.45 | 0.47 |
| (N = 8) | Effect (%) | — | — | 44.6 | 73.2 | 82.2 | 16.2 |

[a]Withdrawal threshold of the right hind paw to mechanical stimulation measured by von Frey filaments (g)
[b]Baseline was measured prior to the first injection of acidic saline.
[c]The test compound was tested 7 or 8 days after second administration of acidic saline.
[d]$p < 0.05$, values at 0 hour by one-way ANOVA and Dunnett's test
[e]$p < 0.01$, values at 0 hour by one-way ANOVA and Dunnett's test From the above results, it was confirmed that the test compound showed a significant effect in the fibromyalgia disease model.

What is claimed is:

1. A method for treating fibromyalgia in a subject, comprising:
   administering a therapeutically effective amount of a carbamic acid (R)-1-(2-chlorophenyl)-2-tetrazol-2-yl) ethyl ester of Formula 2, or a pharmaceutically acceptable salt, solvate or hydrate thereof to the subject:

[Formula 2]

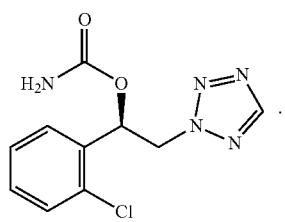

2. The method according to claim 1, wherein the fibromyalgia is selected from the group consisting of fibromyositis, fibrositis, muscular rheumatism, musculoskeletal pain syndrome, non-articular rheumatism, pain due to rheumatoid muscularitis, tension myalgia, hyperalgesia, persistent pain, stiffness and tenderness.

3. The method according to claim 1, wherein the subject is a mammal.

4. The method according to claim 3, wherein the mammal is a human.

5. The method according to claim 1, wherein the therapeutically effective amount of the carbamic acid (R)-1-(2-chlorophenvl)-2-tetrazol-2-yl)ethyl ester of Formula 2 is 50 to 500 mg based on once-daily administration.

6. The method according to claim 1, wherein the carbamic acid (R)-1-(2-chlorophenyl)-2-tetrazol-2-yl)ethyl ester of Formula 2 or a pharmaceutically acceptable salt, solvate or hydrate thereof is administered orally, parenterally, intravenously, intramuscularly, subcutaneously or rectally.

* * * * *